United States Patent [19]
Alfano et al.

[11] Patent Number: 5,983,125
[45] Date of Patent: *Nov. 9, 1999

[54] METHOD AND APPARATUS FOR IN VIVO EXAMINATION OF SUBCUTANEOUS TISSUES INSIDE AN ORGAN OF A BODY USING OPTICAL SPECTROSCOPY

[75] Inventors: Robert R. Alfano, Bronx, N.Y.; Yury Budansky, Oakland, N.J.

[73] Assignee: The Research Foundation of City College of New York

[ * ] Notice: Under 35 U.S.C. 154(b), the term of this patent shall be extended for 832 days.

[21] Appl. No.: 08/522,827

[22] Filed: Sep. 1, 1995

Related U.S. Application Data

[63] Continuation of application No. 08/166,196, Dec. 13, 1993, abandoned.

[51] Int. Cl.$^6$ .................................................. A61B 5/00
[52] U.S. Cl. ........................... 600/473; 600/478; 600/567
[58] Field of Search .................................... 128/633, 634, 128/661, 665, 754; 604/164; 600/310, 317, 342, 473, 475–478, 567

[56] References Cited

U.S. PATENT DOCUMENTS

| | | | |
|---|---|---|---|
| 5,031,634 | 7/1991 | Simon | 128/754 |
| 5,131,398 | 7/1992 | Alfano et al. | 128/665 |
| 5,246,424 | 9/1993 | Wilk | 604/164 |
| 5,263,937 | 11/1993 | Shipp | 604/164 |
| 5,280,788 | 1/1994 | Janes et al. | 128/665 |

*Primary Examiner*—Ruth S. Smith
*Attorney, Agent, or Firm*—Kriegsman & Kriegsman

[57] ABSTRACT

Method and apparatus for examining subcutaneous tissues inside organs of the body. The method comprises the steps of (a) providing an optic probe positioning assembly comprising a solid needle and a hollow tube, the solid needle being sheathed inside the hollow tube; (b) subcutaneously inserting the positioning assembly into a tissue sample to be examined; (c) removing the solid needle from the tissue sample, leaving the hollow tube in place in the tissue; (d) then, inserting an optic probe through the hollow tube into proximity with the tissue sample; (e) optically determining the condition of the tissue sample using the optic probe; (f) after the optically determining step, removing the optic probe from the hollow tube; (g) then, inserting a biopsy needle into the hollow tube; (h) then, excising at least a portion of the tissue sample; and (i) then, removing the biopsy needle and the excised tissue sample from the hollow tube.

6 Claims, 7 Drawing Sheets

1) POSITIONING OF HOLLOW
   TUBE WITH NEEDLE

2) REMOVAL OF NEEDLE

3) INSERTION OF OPTICAL
   PROBE FOR EVALUATION
   AT DIFFERENT DEPATH

4) REMOVAL OF OPTICAL
   PROBE

5) BIOPSY

6) REMOVAL OF SAMPLE
   TISSUES FOR PATHOLOGY

METHOD AND APPARATUS FOR IN VIVO EXAMINATION OF SUBCUTANEOUS TISSUES INSIDE AN ORGAN OF A BODY USING OPTICAL SPECTROSCOPY

This application is a continuation of application Ser. No. 08/166,196 filed on Dec. 13, 1993, now abandoned.

BACKGROUND OF THE INVENTION

The present invention relates to the examination of tissues for indications of disease therein.

Breast, ovarian and cervical cancers are serious diseases that affect over 193,000 women per year. Hence, early detection and treatment of such cancers are important. It is well known that mammographic screening is a key tool in the early detection of breast cancers and that the early detection of breast cancer can reduce the likelihood of death caused by breast cancer. One limitation to the utility of mammography is that benign and malignant lesions oftentimes have similar morphology and are difficult to distinguish based solely on the results of a mammogram. Ovarian cancers are hard to diagnose. Consequently, biopsy is often the only certain way to distinguish between benign and malignant tumors. Biopsy is a surgical procedure performed in a hospital and, hence, is tedious, time-consuming, and expensive. Moreover, most biopsied tumors are found to be benign. Consequently, it is often difficult to determine whether the correct specimen is being biopsied unless the specimen includes a visible lesion.

Therefore, there is clearly a need for a real-time technique for examining tissues and organs in situ without first requiring that a biopsy be performed thereon to correctly identify particular tissues of interest within an organ or on the surface of mucosa.

Optical spectroscopy may play an important role in such an examination technique and may be used to monitor tissue changes before, during and after chemotherapy and/or radiation therapy. For example, native fluorescence spectroscopy and Raman spectroscopy offer new possible methods for detection and characterization of physical, chemical and structural changes in diseased tissue, for either in vivo or in vitro applications of the mucosa layers.

In U.S. Pat. No. 5,131,398 to Alfano et al., which issued Jul. 21, 1992 and which is incorporated herein by reference, there is disclosed a method and apparatus for distinguishing cancerous tumors and tissue from benign tumors and tissue or normal tissue using native fluorescence. The mucosa tissue surface to be examined is excited with a beam of monochromatic light at 300 nanometers (nm). The intensity of the native fluorescence emitted from the tissue is measured at, for example, 340 and 440 nm. The ratio of the two intensities is then calculated and used as a basis for determining if the tissue is cancerous as opposed to benign or normal. The patent is based on the discovery that when tissue is excited with monochromatic light at 300 nm, the native fluorescence spectrum over the region from about 320 nm to 600 nm is substantially different for cancerous tissue than for benign tumors and tissue or normal tissue.

In U.S. Pat. No. 5,261,410 to Alfano et al., which issued Nov. 16, 1993 and which is incorporated herein by reference, there is disclosed a method for determining if a tissue is a malignant tumor tissue, a benign tumor tissue, or a normal or benign tissue. The method is based on the discovery that, when irradiated with a beam of infrared, monochromatic light, malignant tumor tissue, benign tumor tissue, and normal or benign tissue produce distinguishable Raman spectra. For human breast tissue, some salient differences in the respective Raman spectra are the presence of four Raman bands at a Raman shift of about 1078, 1300, 1445 and 1651 $cm^{-1}$ for normal or benign tissue, the presence of three Raman bands at a Raman shift of about 1240, 1445 and 1659 $cm^{-1}$ for benign tumor tissue, and the presence of two Raman bands at a Raman shift of about 445 and 1651 $cm^{-1}$ for malignant tumor tissue. In addition, it was discovered that for human breast tissue the ratio of intensities of the Raman bands at a Raman shift of about 1445 and 1659 $cm^{-1}$ is about 1.25 for normal or benign tissue, about 0.93 for benign tumor tissue, and about 0.87 for malignant tumor tissue.

The above-described methods rely on emissions from the surfaces of photoexcited mucosa.

SUMMARY OF THE INVENTION

It is an object of the present invention to provide a new technique for examining subcutaneous tissues for indications of disease therein.

It is another object of the present invention to provide a technique as described above which can be used to quickly and correctly identify desired subcutaneous tissue specimens inside an organ, for example, those in need of futher evaluation (e.g. biopsy) and/or treatment. The structure as well as molecular content of chromophors and fluorophors are different in spatial extent and path in an organ.

It is still another object of the present invention to provide a technique as described above which involves the use of optical spectroscopy to examine a tissue inside an organ.

Additional objects, as well as features and advantages thereof, will be set forth in part in the description which follows, and in part will be obvious from the description or may be learned by practice of the invention. The objects of the invention also may be realized and attained by means of instrumentalities and combinations particularly pointed out in the appended claims.

According to one embodiment of the present invention, optical examination of a subcutaneous tissue inside an organ is accomplished by use of an apparatus which preferably comprises (a) a light source; (b) means for measuring the intensity of light at a first wavelength; (c) means for measuring the intensity of light at a second wavelength; (d) an assembly comprising (i) a hollow needle having a light transmissive tip, and (ii) an optic fiber bundle having a first end and a second end, said first end being inserted into the hollow needle, said second end having a first leg optically coupled to said light source to transmit light therefrom to the subcutaneous tissue and having second and third legs for transmitting light collected from the illuminated subcutaneous tissue to said means for measuring the intensity of light at said first wavelength and said means for measuring the intensity of light at said second wavelength, respectively; and (e) means for determining the condition of the subcutaneous tissue based on the intensity measurements at said first and second wavelengths.

Preferably, said determining means comprises means for taking a ratio of the intensities at said first and second wavelengths and a computer for comparing the ratio thus calculated to appropriate standards. The results of the comparison may be displayed on a monitor or printed out.

Preferably, to assist in the insertion and proper placement of the hollow needle/fiber optic bundle assembly in or near the tissue to be tested, a solid needle sheathed in a hollow tube is inserted into the patient's organ prior to insertion of the needle/fiber optic bundle assembly thereinto. The solid needle is then removed, with the hollow tube remaining in place in the patient, and the needle/fiber optic bundle assembly is then inserted into the hollow tube to evaluate an organ at a given depth. An organ can be breast, brain, kidney, liver, lung, gynecological tract, etc.

As can readily be appreciated, after optically examining a tissue sample in the manner described above, the needle/fiber optic bundle assembly may be removed from the hollow tube, and a biopsy needle may be inserted thereinto for removal of a tissue sample from the organ.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
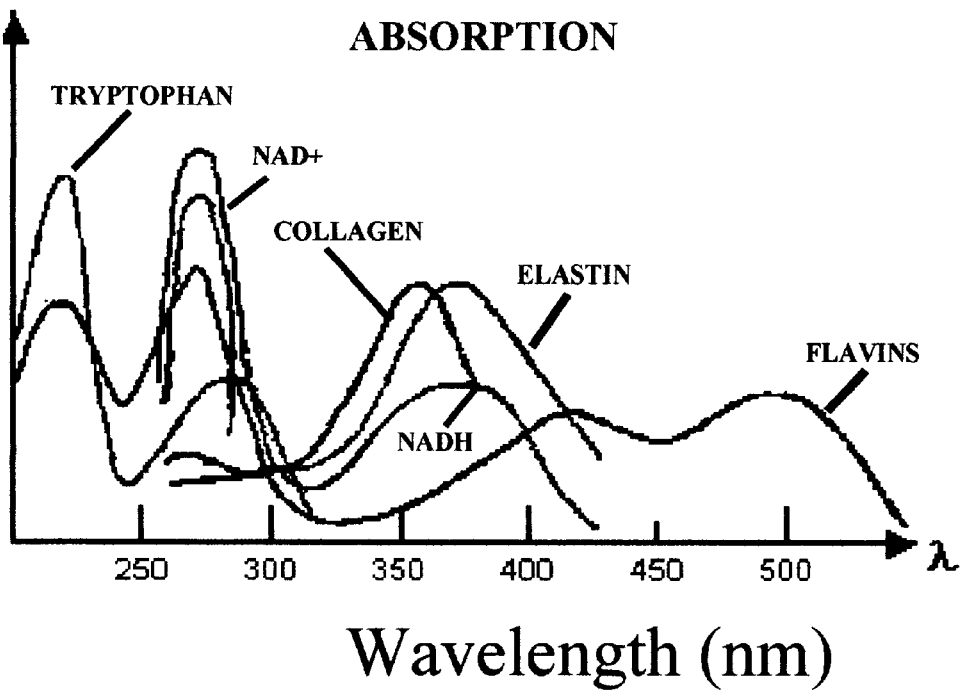
FIG. 1 is a graph depicting the absorption spectra of several fluorophors native to subcutaneous organ tissues.
Figure 2:
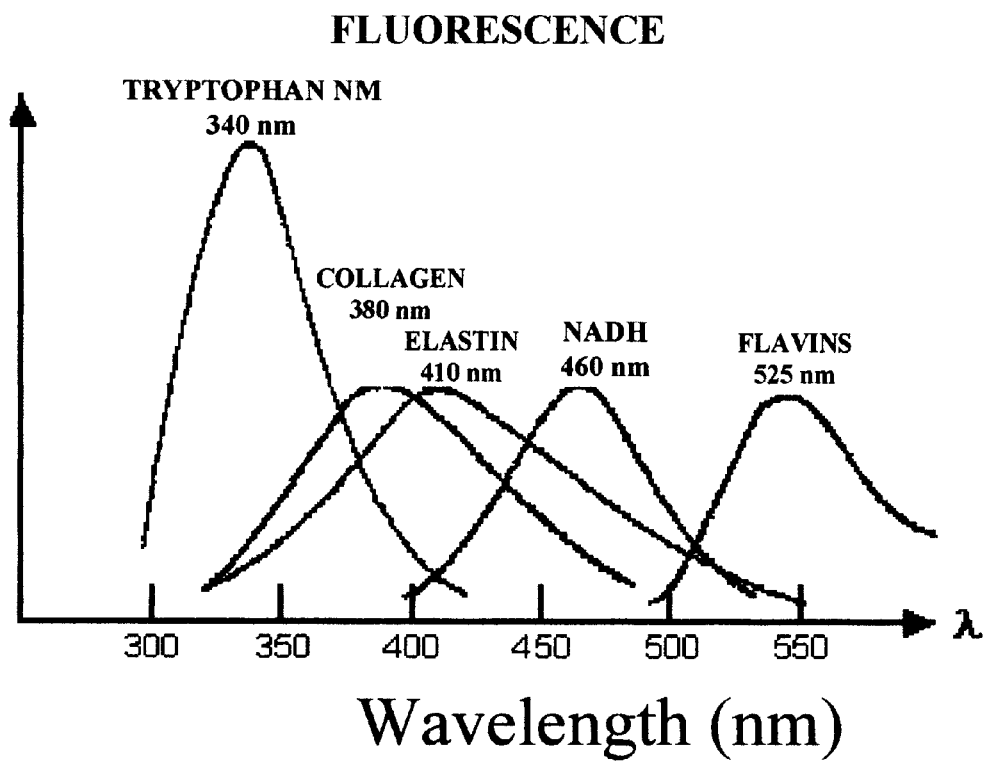
FIG. 2 is a graph depicting the fluorescence spectra of several fluorophors native to subcutaneous organ tissues.

The fluorescence and absorption spectral properties of certain disease-indicative fluorophors (e.g., tryptophan, collagen, elastin, NADH, and flavin) which are native to subcutaneous tissues are shown in FIGS. 1 and 2. As can be seen in FIG. 2, when, for example, an excitation wavelength of 340 nm is used, collagen and elastin emit fluorescence at 380 nm and NADH, collagen and elastin emit fluorescence at 460 nm.

Figure 3:
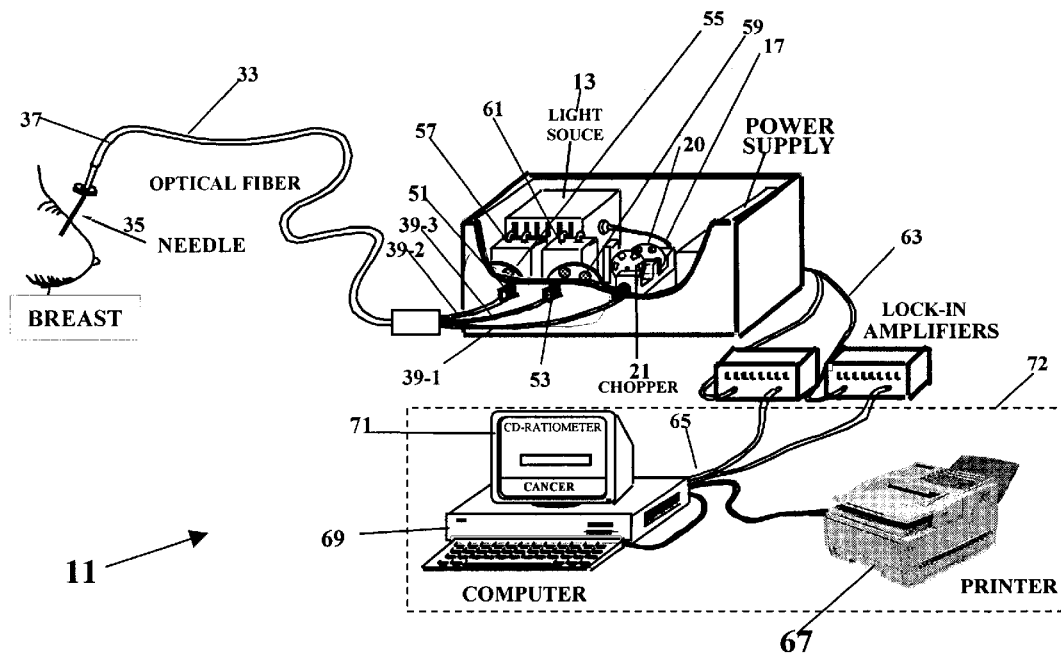
FIG. 3 is a schematic diagram of one embodiment of an apparatus for examining subcutaneous organ tissue samples using optical spectroscopy.
Figure 4:
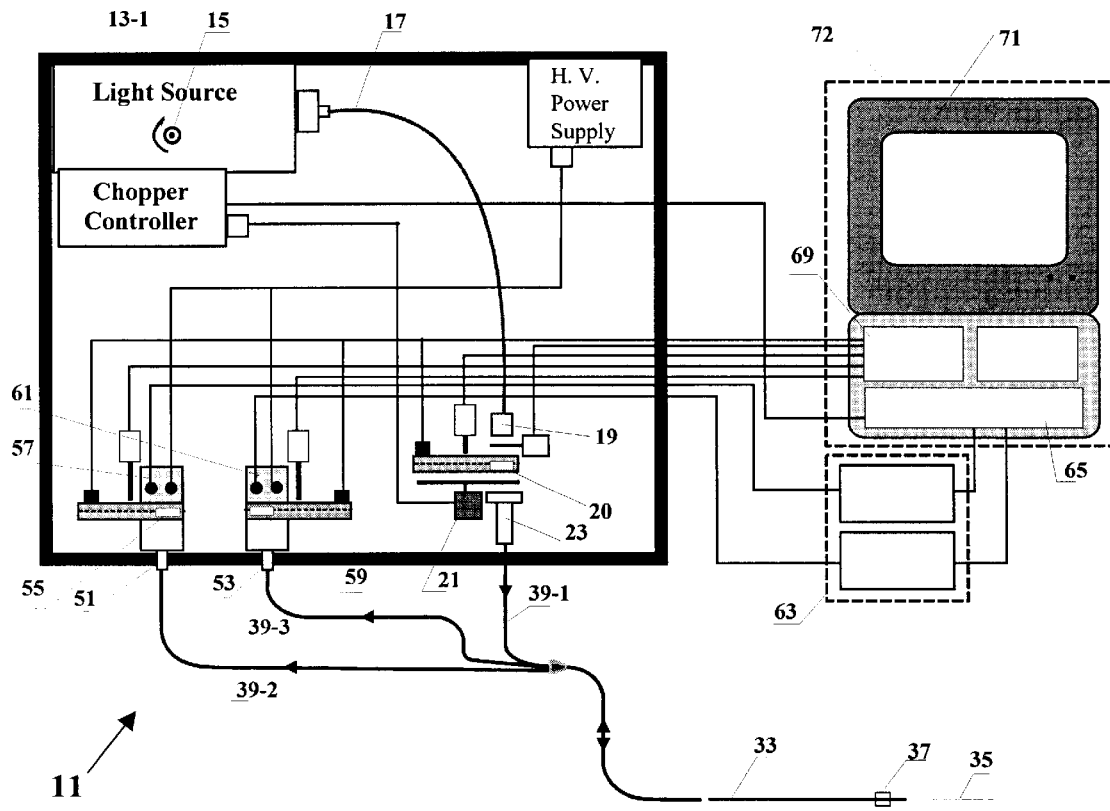
FIG. 4 is a block diagram of the apparatus of FIG. 3.

Referring now to FIGS. 3 and 4, there are shown schematic and block diagrams of one embodiment of an apparatus constructed according to the teachings of the present invention for examining subcutaneous tissues using optical spectroscopy, the apparatus being represented generally by reference numeral 11.

Apparatus 11 comprises a light source 13. As shown in FIG. 4, because apparatus 11 is configured for fluorescence based applications, light source 13 preferably includes a xenon lamp 15, a fused silica (quartz) fiber bundle 17 into which the light from lamp 15 is focused, a collimator 19 for collimating the light emergent from bundle 17, a 300 nm filter 20 for selecting an excitation wavelength of 300 nm, a chopper 21 for modulating the filtered light and reducing the noise from ambient light and a second collimator 23 for focusing the modulated light into the excitation leg of an optic fiber (quartz) bundle to be described below.

As can readily be appreciated, where apparatus 11 is configured for Raman based applications, a light source comprising, for example, a semiconducting laser operating at about 800 nm could be used instead of the arrangement described above.

Apparatus 11 also includes an assembly 31 comprising an optic fiber bundle 33 and a hollow needle 35. A first end 37 of bundle 33 is inserted into needle 35, and the opposite end of bundle 33 is trifurcated into three legs 39-1, 39-2 and 39-3. First end 37 of bundle 33 preferably has a diameter of 1–2 mm and a length of approximately 150 cm (and may be sheathed in a thin metal jacket of 10 to 20 cm). The core of bundle 33, which is derived from leg 39-1, is preferably a quartz fiber with a diameter of 0.4 mm. The transmission of the core fiber is designed to be about 80% for 300 nm light. The core fiber is preferably surrounded by many smaller diameter (e.g., less than 0.2 mm diameter and preferably 0.05 to 0.1 mm diameter) quartz fibers which are equally divided into legs 39-2 and 39-3. The effective transmission area of each of legs 39-2 and 39-3 is preferably about 1.5 mm$^2$, and the transmission of each of legs 39-2 and 39-3 is designed to be about 40%.

Excitation light from light source 13 is transmitted to a desired subcutaneous tissue sample via leg 39-1 of bundle 33. The resultant fluorescence from the excited tissue sample is collected by the smaller diameter quartz fibers in bundle 33 and transmitted through legs 39-2 and 39-3.

Apparatus 11 further comprises means 51 for measuring the intensity of light at a first wavelength and means 53 for measuring the intensity of light at a second wavelength, means 51 and means 53 being disposed at the respective outputs of legs 39-2 and 39-3. In the present embodiment, means 51 comprises a narrow band filter 55 positioned in front of a photomultiplier tube 57, and means 53 comprises a narrow band filter 59 positioned in front of a photomultiplier tube 61. Preferably, one of filters 55 and 59 is selective for light of 340 nm and the other is selective for light of 440 nm. (It should be understood that filters selective for fluorescence wavelengths other than 340 nm and 440 nm may be used and that, in those instances in which Raman spectroscopy is employed, filters selective for Raman shifts, such as 1250 cm$^{-1}$, 1450 cm$^{-1}$ and 1650 cm$^{-1}$, can be used). The outputs from photomultiplier tubes 57 and 61 are fed into an analog to digital converter 63 having two outputs. One output is fed into a ratiometer 65 where a ratio of the signals from photomultiplier tubes 57 and 61 is taken. This ratio is then displayed using a recorder or printer 67. The other output is fed into a computer 69 which also takes a ratio of the two photomultiplier tube signals and compares the ratio to a pre-set value. The result of this comparison is then displayed on the computer monitor 71 (or alternatively could be printed out using a recorder or printer). Ratiometer 65, recorder 67, computer 69 and printer 71 are collectively represented in FIGS. 3 and 4 by reference numeral 72.

Figure 5A:
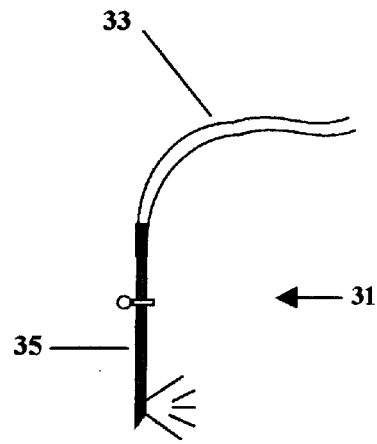
FIGS. 5(a) and 5(b) are fragmentary schematic views of the probing end of the hollow needle/fiber optic bundle assembly shown in FIG. 3.
Figure 5B:
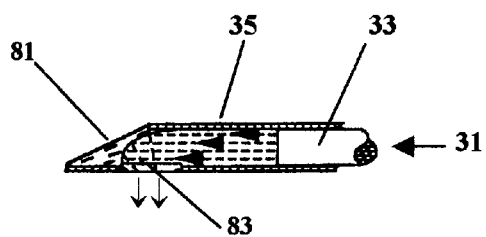

Referring now to FIGS. 5(a) and 5(b), there are shown more detailed views of the probing end of assembly 31. As can be seen best in FIG. 5(b), needle 35 is provided with a curved or plane mirror 81 for reflecting the light emitted from quartz fiber bundle 33 at a 90 degree angle and a quartz window 83 through which the 90 degree reflected light is transmitted to the tissue sample. One advantageous feature associated with this construction is that an entire area can be examined by rotating assembly 31 about its longitudinal axis like a periscope.

Figure 6A:
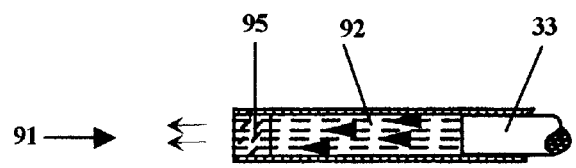
FIGS. 6(a) and 6(b) are fragmentary schematic views of alternative embodiments of the hollow needle/fiber optic bundle assembly shown in FIGS. 5(a) and 5(b)
Figure 6B:
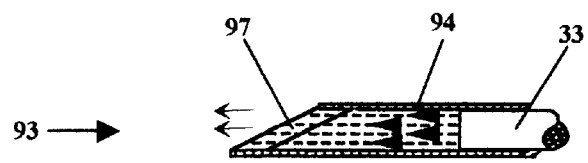

FIGS. 6(a) and 6(b) illustrate alternative hollow needle/fiber quartz optic fiber bundle assemblies 91 and 93, respectively. Needles 92 and 94, respectively, of assemblies 91 and 93 do not include a mirror and excite tissue samples at 0 degrees through quartz windows 95 and 97, respectively. Assembly 91 is designed for large area tissue sampling, and assembly 93 is designed for small area tissue sampling.

Referring now to FIGS. 7(a) through 7(f), a six step procedure is illustrated for examining a subcutaneous organ tissue, such as inside the breast, the brain, the GYN tract (e.g., ovary), etc., for cancer in accordance with the teachings of the present invention.

Figure 7A:
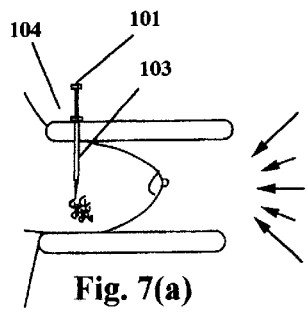
FIGS. 7(a) through 7(f) are fragmentary schematic views illustrating a procedure by which subcutaneous tissue inside an organ (e.g., breast) may be examined in accordance with the teachings of the present invention.

In FIG. 7(a), a solid metal needle 101 fitted inside a hollow tube 103 (needle 101 and tube 103 collectively being referred to herein as an optic probe positioning assembly 104) is inserted into the tissue to be sampled under mammographic X-ray guidance to the tumor growth.

Figure 7B:
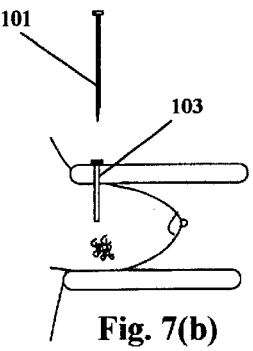

In FIG. 7(b), solid metal needle 101 is removed, leaving hollow tube 103 in place in the tissue.

Figure 7C:
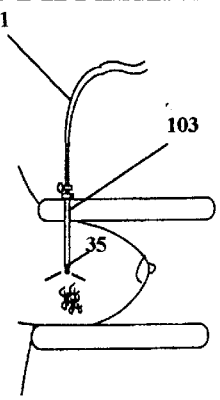

In FIG. 7(c), assembly 31 is inserted into hollow tube 103 until the tip of needle 35 is in contact with or in close proximity to the tissue to be tested, and apparatus 11 is used to examine the tissue for cancer in the manner described above.

Figure 7D:
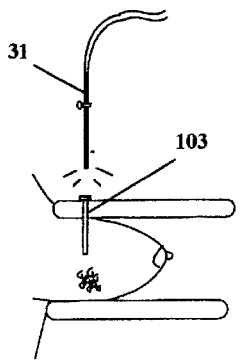

In FIG. 7(d), assembly 31 is removed from hollow tube 103.

Figure 7E:
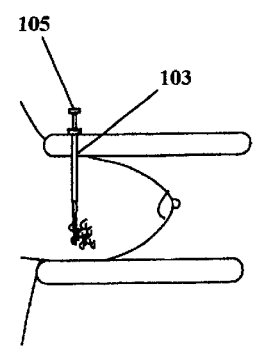

In FIG. 7(e), a biopsy needle 105 is inserted into hollow tube 103 and is used to cut out a piece of the tissue sample.

Figure 7F:
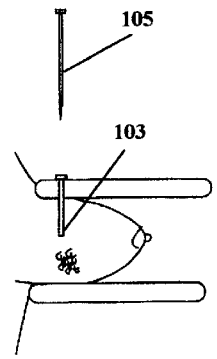

In FIG. 7(f), biopsy needle 105 and the excised tissue sample are removed from the breast for pathology.

It is envisioned that, for a comparison with non-malignant tissue in the same breast, the procedure described above will be used to obtain both fluorescence ratio measurements and biopsy samples at different distances and in each of several tracks in the breast being examined. By using several tracks of different lengths and orientations leading to a tumor, a ratio map down a track can be made and compared with results from pathology. The measurement process for optical sampling of a tumor is expected to require about one minute for each position. The ratios can be printed and stored for tumor and inside organs analysis.

Figure 8A:
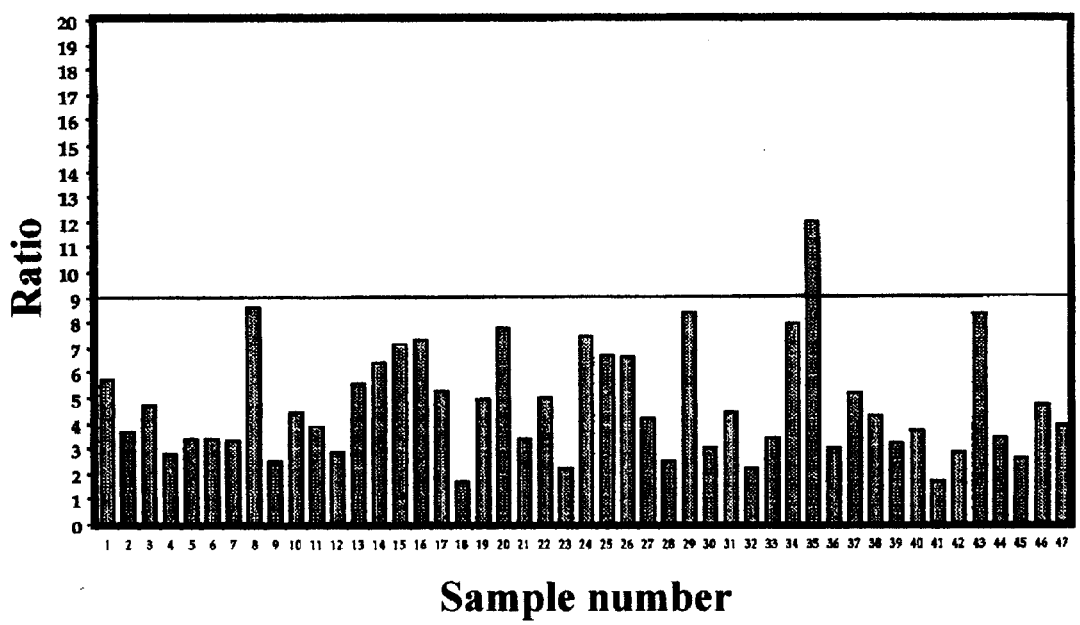
FIGS. 8(a) and 8(b) are histograms of the ratios of fluorescence intensities at 340 nm and 440 nm for 47 benign and normal breast tissue samples and 40 cancerous breast tissue samples, respectively.
Figure 8B:
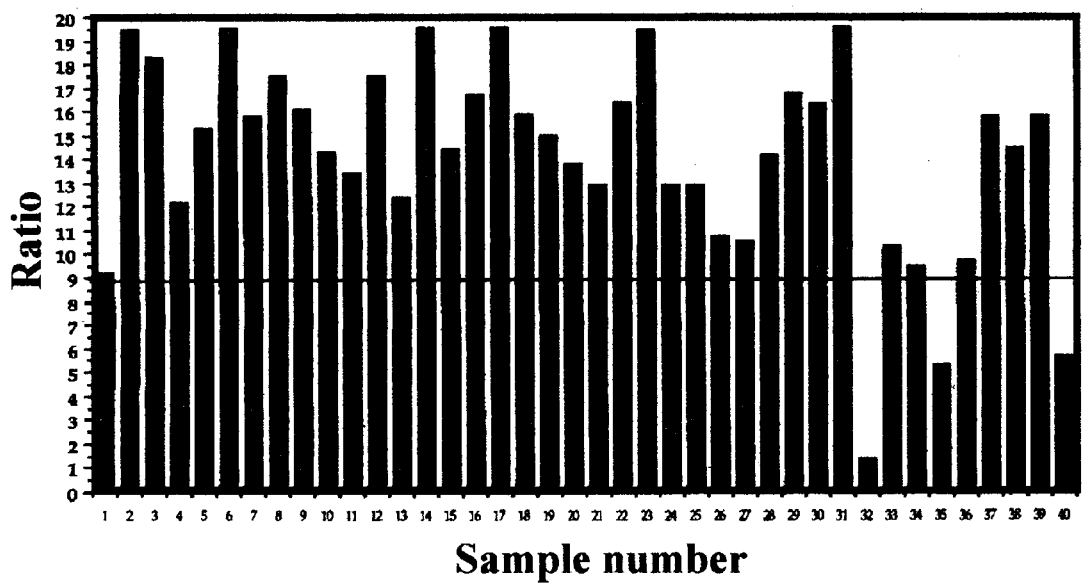

It is expected that the criteria to separate malignant and benign tissues using the present invention will be established soon and will be checked against the in vitro ratio of 9 (cancer>9; normal<9) which is the experimental value for in vitro breast tissues. See FIGS. 8(a) and 8(b) which are the respective histograms for non-malignant and malignant breast tissue samples. The information found in these histograms is summarized in Table I below.

TABLE I

| Parameter | Cancer | Normal or Benign |
|---|---|---|
| No. of samples | 40 | 47 |
| Sensitivity | 37/40 = 92.5% | — |
| False Negative | 3/40 = 7.5% | — |
| Specificity | — | 46/47 = 98% |
| False Positive | — | 1/47 = 2% |

As can readily be appreciated, the ratio value for distinguishing cancerous from non-cancerous tissues may be different in vivo and for different organs, such as the brain.

Table II lists the measured ratio K1 values from malignant and non-malignant GYN tissues with an excitation wavelength of 300 nm (K1=l(340nm)/l(440nm)).

TABLE II

| No. | Non-malignant Tissues | K1 | Malignant Tissues | K1 |
|---|---|---|---|---|
| 1 | Ovary | 7.0 | Endometrium | 23.0 |
| 2 | Cervix | 11.0 | Cervix | 21.0 |
| 3 | Ovary | 6.5 | Ovary | 14.0 |
| 4 | Cervix | 7.6 | Cervix | 12.0 |
| 5 | Cervix | 10.4 | Endometrium | 12.0 |
| 6 | Myometrium | 7.6 | Ovary | 19.0 |
| 7 | Uterus | 5.4 | Ovary | 16.0 |
| 8 | Myometrium | 8.1 | Endometrium | 14.0 |
| 9 | Cervix Benign | 5.7 | Cervix | 12.0 |
| 10 | Cervix Benign | 5.8 | Endometrium | 35.0 |
| 11 | Uterus | 2.8 | Ovary | 35.0 |
| 12 | Ovary | 5.7 | Endometrium | 35.0 |
| 13 | Uterus | 9.5 | Myometrium | 35.0 |
| 14 | Uterus | 18.1 | Ovary | 35.0 |
| 15 | Uterus | 9.51 | Endometrium | 16.0 |
| 16 | Cervix | 4.55 | Endometrium | 29.0 |
| 17 | Cervix | 13.30 | Ovary | 33.0 |
| 18 | Cervix | 6.05 | Uterus | 20.0 |
| 19 | Cervix | 10.38 | Endometrium | 10.0 |
| 20 | Ovary | 11.40 | Cervix | 12.0 |
| 21 | Uterus | 9.56 | Uterus | 18.0 |
| 22 | Vagina | 8.96 | Uterus | 18.0 |
| 23 | Cervix | 5.20 | Ovary | 27.4 |
| 24 | Ovary | 12.8 | Endometrium | 12.4 |
| 25 | | | Cervix | 16.00 |
| 26 | | | Endometrium | 8.40 |
| 27 | | | Myometrium | 23.50 |
| 28 | | | Myometrium | 18.45 |
| 29 | | | Endometrium | 15.45 |
| 30 | | | Uterus | 22.20 |
| 31 | | | Ovary | 20.10 |
| 32 | | | Ovary | 22.00 |
| 33 | | | Uterus | 16.75 |
| 34 | | | Cervix | 25.90 |
| 35 | | | Uterus | 25.90 |
| 36 | | | Uterus | 17.20 |
| 37 | | | Vagina | 29.10 |
| 38 | | | Ovary | 25.80 |
| 39 | | | Uterus | 24.80 |
| 40 | | | Ovary | 16.40 |
| 41 | | | Cervix | 14.47 |
| 42 | | | Uterus | 20.10 |
| 43 | | | Cervix | 23.80 |
| 44 | | | Uterus | 28.39 |
| 45 | | | Uterus | 12.80 |
| 46 | | | Cervix | 17.87 |
| 47 | | | Uterus | 30.00 |
| 48 | | | Uterus | 28.67 |
| 49 | | | Uterus | 27.64 |
| 50 | | | Ovary | 25.75 |
| 51 | | | Ovary | 16.70 |
| 52 | | | Uterus | 21.43 |
| 53 | | | Omentum | 38.27 |
| 54 | | | Uterus | 22.11 |
| 55 | | | Myometrium | 27.02 |
| 56 | | | Uterus | 20.56 |
| 57 | | | Cervix | 23.2 |
| 58 | | | Uterus | 27.16 |
| 59 | | | Tubn | 27.1 |
| 60 | | | Endometrium | 25.02 |
| 61 | | | Ovary | 25.8 |
| 62 | | | Uterus | 18.30 |
| 63 | | | Endometrium | 21.40 |
| 64 | | | Ovary | 20.13 |
| 65 | | | Uterus | 29.30 |
| Standard | | <11.50 | | >11.50 |
| False Negative | | | | 2 |
| False Positive | | 3 | | |
| Sensitivity | | | | 96% |
| Specificity | | 90% | | |

Figure 9A:
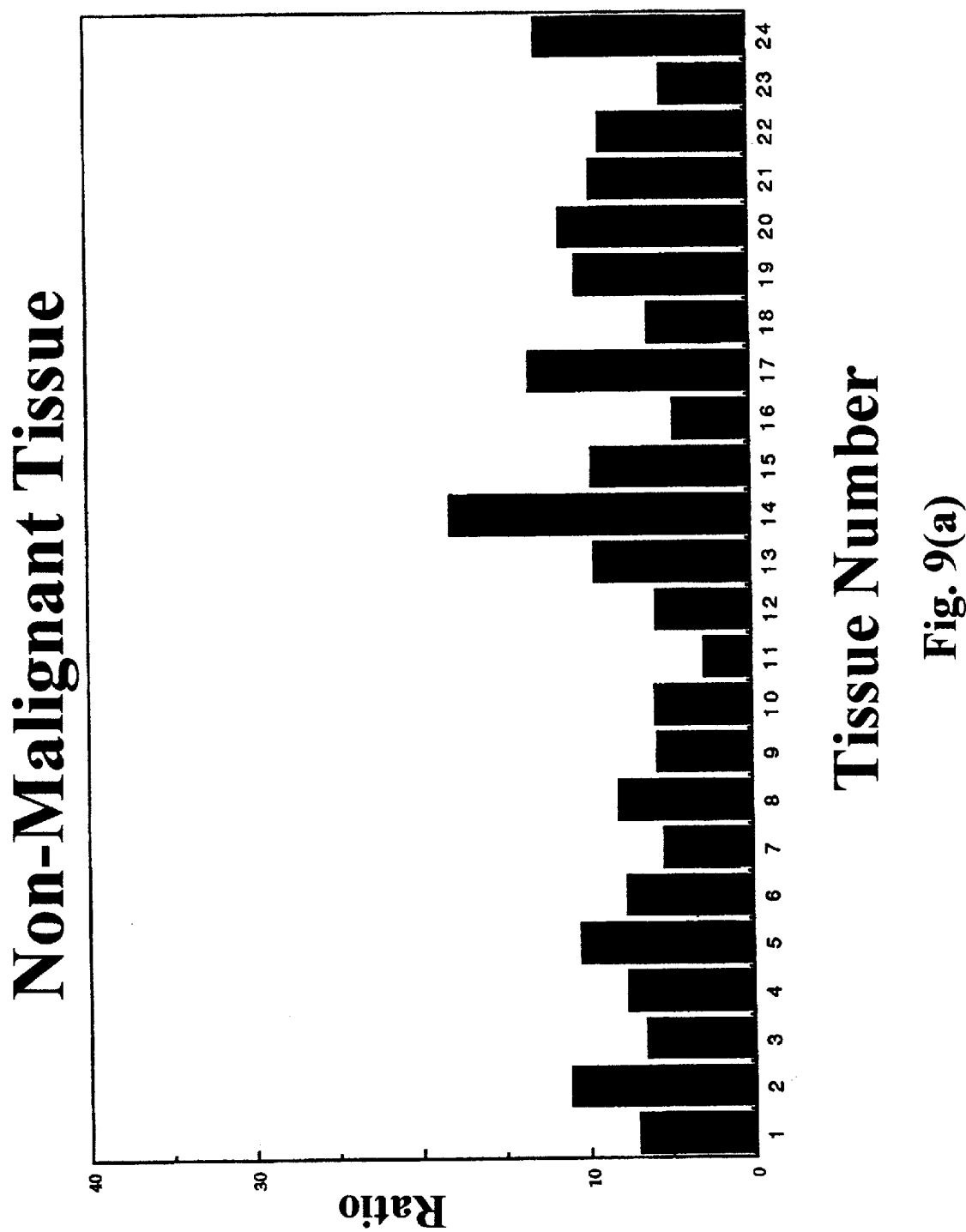
FIGS. 9(a) and 9(b) are histograms of the ratios of fluorescence intensities at 340 nm and 440 nm for the non-malignant and malignant GYN tissue samples, respectively, which appear in Table II.
Figure 9B:
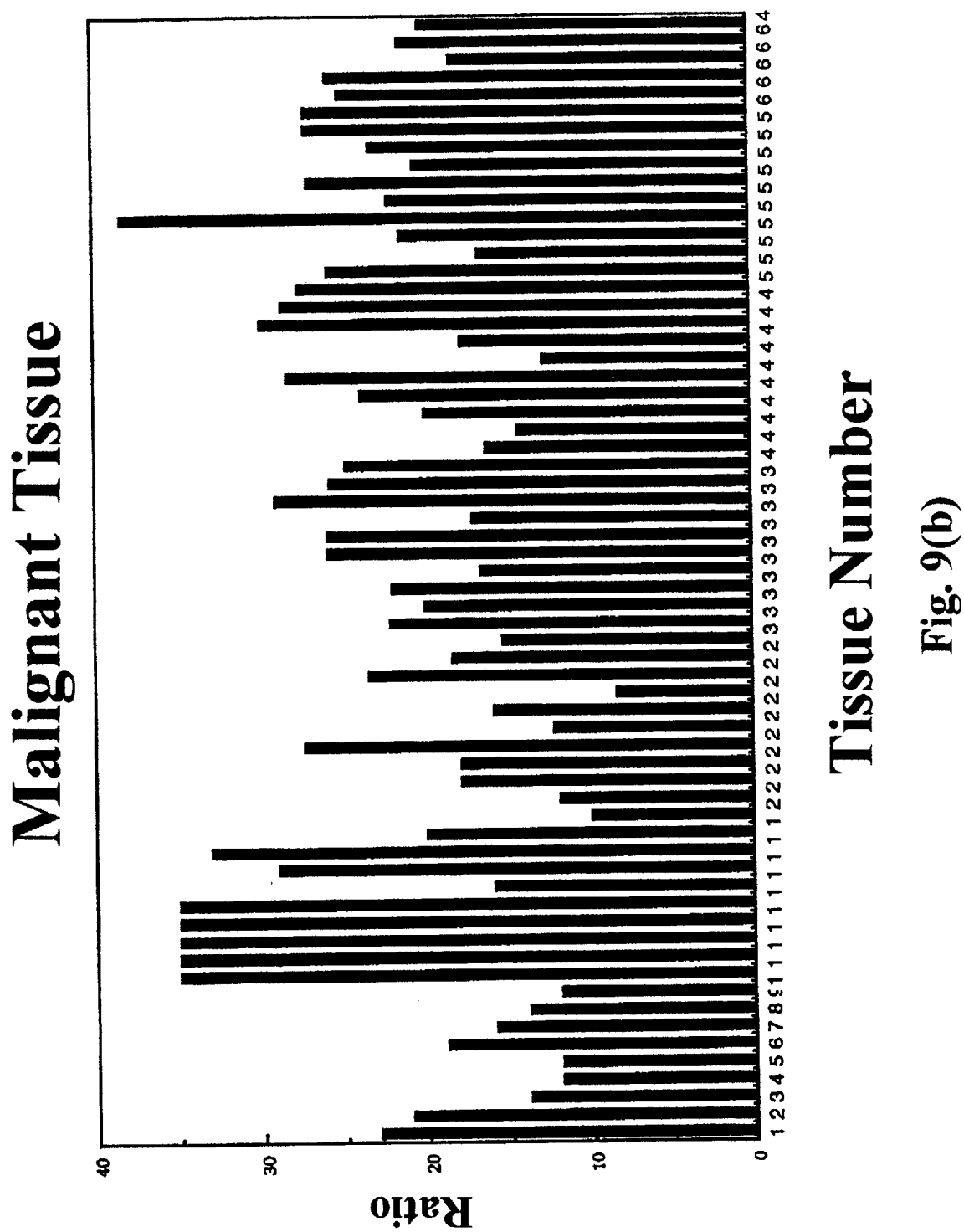

Much of the information appearing in Table II is also shown in FIGS. 9(a) and 9(b), which are histograms of the ratios for the non-malignant and malignant GYN tissue samples, respectively.

The exact ratio criterion will depend on clinical testing and organ type. This approach can be used with and without pathology once it has been tested to be as accurate as pathology.

It is to be understood that apparatus 11 could be used for in vitro as well as in vivo applications. It should also be noted that the present invention is not limited to the examination of breast tissues and may be used, for example, to examine other organ tissues derived from, for example, the liver, prostate, kidney, brain, lung, and chest wall. The present invention also may be used to examine tissues for disease states other than cancer inside an organ.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of examining a subcutaneous tissue sample comprising the steps of:
   (a) providing an optic probe positioning assembly comprising a solid needle and a hollow tube, said solid needle being sheathed inside said hollow tube;
   (b) subcutaneously inserting said positioning assembly into a tissue sample to be examined;
   (c) removing said solid needle from the tissue sample, leaving said hollow tube in place in the tissue;
   (d) then, inserting an optic probe through the hollow tube into proximity with the tissue sample, said optic probe comprising
   (i) an optic fiber bundle for use in transmitting light to and from the tissue sample, said optic fiber bundle having a longitudinal axis, and
   (ii) a hollow needle, said optic fiber bundle disposed coaxially within said hollow needle, said hollow needle having a mirror for reflecting light transmitted to and from said optic fiber bundle at approximately a 90 degree angle relative to the longitudinal axis of said optic fiber bundle and having a window through which said reflected light may pass;
   (e) optically determining the condition of the tissue sample using said optic probe;
   (f) after said optically determining step, removing said optic probe from said hollow tube;
   (g) then, inserting a biopsy needle into said hollow tube;
   (h) then, excising at least a portion of the tissue sample; and
   (i) then, removing said biopsy needle and the excised tissue sample from the hollow tube.

2. The method as claimed in claim 1 wherein said optically determining step comprises determining the condition of the tissue sample using fluorescence spectroscopy.

3. The method as claimed in claim 1 wherein said optically determining step comprises determining the condition of the tissue sample using Raman spectroscopy.

4. The method as claimed in claim 1 wherein the subcutaneous tissue sample is breast tissue.

5. The method as claimed in claim 1 wherein the subcutaneous tissue sample inside an organ is selected from the group consisting of the liver, the prostate, the kidney, the brain, the lungs, the GYN tract and the chest wall.

6. The method as claimed in claim 1 further comprising, after removing the excised tissue sample from the hollow tube, performing a biopsy on the excised tissue sample.

* * * * *